United States Patent [19]

Ewen et al.

[11] Patent Number: 4,892,851
[45] Date of Patent: Jan. 9, 1990

[54] PROCESS AND CATALYST FOR PRODUCING SYNDIOTACTIC POLYOLEFINS

[75] Inventors: John A. Ewen, Houston; Abbas Razavi, Seabrook, both of Tex.

[73] Assignee: Fina Technology, Inc., Dallas, Tex.

[21] Appl. No.: 220,007

[22] Filed: Jul. 15, 1988

[51] Int. Cl.$^4$ .................. C08F 4/62; C08F 4/64; C08F 4/68
[52] U.S. Cl. .................. 502/104; 502/117; 502/103; 556/43; 556/53; 556/58; 526/160
[58] Field of Search .................. 556/43, 53, 58; 502/103, 117, 104

[56] References Cited

U.S. PATENT DOCUMENTS

| | | | |
|---|---|---|---|
| 3,258,455 | 6/1986 | Natta et al. | 260/93.7 |
| 3,268,627 | 8/1986 | Emrick et al. | 260/897 |
| 3,305,538 | 2/1967 | Natta et al. | 260/93.7 |
| 3,364,190 | 1/1968 | Emrick et al. | 260/93.7 |
| 4,411,821 | 10/1983 | Howard, Jr. | 502/117 |
| 4,497,906 | 2/1985 | Hanji et al. | 502/117 X |
| 4,522,982 | 6/1985 | Ewen | 525/240 |
| 4,530,914 | 7/1985 | Ewen et al. | 502/117 X |
| 4,542,199 | 9/1985 | Kaminsky et al. | 502/117 X |
| 4,658,078 | 4/1987 | Slaugh et al. | 502/117 X |
| 4,701,432 | 10/1987 | Welborn | 502/117 X |

FOREIGN PATENT DOCUMENTS

| | | |
|---|---|---|
| A50436 | 11/1985 | Australia . |
| 0128046 | 12/1984 | European Pat. Off. . |
| 0129368 | 12/1984 | European Pat. Off. . |
| 0185918 | 7/1986 | European Pat. Off. . |
| WO87/0299 | 5/1987 | PCT Int'l Appl. . |
| WO87/03604 | 6/1987 | PCT Int'l Appl. . |

OTHER PUBLICATIONS

A. Zambelli, P. Locatelli, A. Rovasoli, and D. R. Ferro, "Correlation between CMR Chemical Shifts and Conformation of Polymers 3, Hexad Sequence Assignments of Methylene Spectra of Polypropylene", Aug. 13, 1979, Macromolecules, 1980, vol. 13, pp. 267-270.

Alan Bunn and Michael E. A. Cudby, "Solid-State High-Resolution CN.m.r. Spectra of Polypropene", J.C.S. Chem. Comm., 1981, pp. 15, 16.

John A. Ewen, "Mechanisms of Stereochemical Control in Propylene Polymerizations with Soluble Group 4B Metallocene/Methylalumoxane Catalysts" Mar. 12, 1984, pp. 6355-6364.

John A. Ewen, "Ligand Effects on Metallocene Catalyzed Ziegler-Natta Polymerizations", published by Elsevier Publishing Co., Apr. 26, 1986, pp. 271-292.

Primary Examiner—Patrick P. Garvin
Attorney, Agent, or Firm—Stuart L. Watt; John K. Abokhair; M. Norwood Cheairs

[57] ABSTRACT

The invention provides a metallocene catalyst for use in preparing syndiotactic polyolefins. The catalyst comprises a bridged metallocene in which one of the cyclopentadienyl rings is substituted in a substantially different manner from the other ring. It was discovered that this type of catalyst is highly syndiospecific, and it also produces a polymer with a novel microstructure. The invention further includes the use of one or more of the catalysts in a polymerization process. The catalyst is generally described by the formula $$R''(CpR_n)(CpR'_m)MeQ_k$$

wherein each Cp is a cyclopentadienyl or substituted cyclopentadienyl ring; each $R_n$ and $R'_m$ is the same or different and is a hydrocarbyl radicals having 1-20 carbon atoms; R" is a structural bridge between the two Cp rings imparting stereoigidity to the catalyst; Me is a group 4b, 5b, or 6b metal from the Periodic Table of Elements; each Q is a hydrocarbyl radical having 1-20 carbon atoms or is a halogen; $0 \leq k \leq 3$; $0 \leq n \leq 4$; $1 \leq m \leq 4$; and wherein $R'_m$ is selected such that $(CpR'_m)$ is a sterically different ring than $(CpR_n)$.

12 Claims, 4 Drawing Sheets

PROCESS AND CATALYST FOR PRODUCING SYNDIOTACTIC POLYOLEFINS

TECHNICAL FIELD

The invention relates to a metallocene catalyst useful in preparing syndiotactic polyolefins. The catalyst consists of a bridged metallocene in which one of the cyclopentadienyl rings is substituted in a different manner from the other ring. The invention further includes a process of preparing syndiotactic polyolefins that comprises the use of one or more of the disclosed catalysts and also a process for preparing the catalysts.

BACKGROUND OF THE INVENTION

The present invention provides a catalyst and process for polymerizing olefins having three or more carbon atoms to produce a polymer with a syndiotactic stereochemical configuration. The catalyst and process are particularly useful in polymerizing propylene to form a highly crystalline, novel microstructure of syndiotactic polypropylene.

As known in the art, syndiotactic polymers have a unique stereochemical structure in which monomeric units having enantiomorphic configuration of the asymmetrical carbon atoms follow each other alternately and regularly in the macromolecular main chain. Syndiotactic polypropylene was first disclosed by Natta et al. in U.S. Pat. No. 3,258,455. The Natta group obtained syndiotactic polypropylene by using a catalyst prepared from titanium trichloride and diethyl aluminum monochloride. A later patent to Natta et al., U.S. Pat. No. 3,305,538, discloses the use of vanadium triacetylacetonate or haloenated vanadium compounds in combination with organic aluminum compounds for producing syndiotactic polypropylene. U.S. Pat. No. 3,364,190 to Emrick discloses a catalyst system composed of finely divided titanium or vanadium trichloride, aluminum chloride, a trialkyl aluminum and a phosphorus-containing Lewis base as producing syndiotactic polypropylene.

As disclosed in these patent references and as known in the art, the structure and properties of syndiotactic polypropylene differ significantly from those of isotactic polypropylene. The isotactic structure is typically described as having the methyl groups attached to the tertiary carbon atoms of successive monomeric units on the same side of a hypothetical plane through the main chain of the polymer, e.g., the methyl groups are all above or below the plane. Using the Fischer projection formula, the stereochemical sequence of isotactic polypropylene is described as follows:

Another way of describing the structure is through the use of NMR. Bovey's NMR nomenclature for an isotactic pentad is ...mmmm... with each "m" representing a "meso" dyad or successive methyl groups on the same side in the plane. As known in the art, any deviation or inversion in the structure of the chain lowers the degree of isotacticity and crystallinity of the polymer.

In contrast to the isotactic structure, syndiotactic polymers are those in which the methyl groups attached to the tertiary carbon atoms of successive monomeric units in the chain lie on alternate sides of the plane of the polymer. Syndiotactic polypropylene is shown in zig-zag representation as follows:

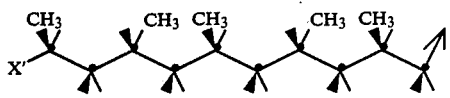

Using the Fischer projection formula, the structure of a syndiotactic polymer is designated as:

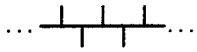

In NMR nomenclature, this pentad is described as ...rrrr... in which each "r" represents a "racemic" dyad, i.e., successive methyl groups on alternate sides of the plane. The percentage of r dyads in the chain determines the degree of syndiotacticity of the polymer. Syndiotactic polymers are crystalline and, like the isotactic polymers, are insoluble in xylene. This crystallinity distinguishes both syndiotactic and isotactic polymers from an atactic polymer that is soluble in xylene. Atactic polymer exhibits no regular order of repeating unit configurations in the polymer chain and forms essentially a waxy product.

While it is possible for a catalyst to produce all three types of polymer, it is desirable for a catalyst to produce predominantly isotactic or syndiotactic polymer with very little atactic polymer. Catalysts that produce isotactic polyolefins are disclosed in copending U.S. Patent Application Ser. Nos. 034,472 filed Apr. 3, 1987 and now abandoned; 096,075 filed Sept. 11, 1987 and now Pat. No. 4,794,096; and 095,755 filed on Sept. 11, 1987 and now abandoned. These applications disclose chiral, stereorigid metallocene catalysts that polymerize olefins to form isotactic polymers and are especially useful in the polymerization of a highly isotactic polypropylene. The present invention, however, provides a different class of metallocene catalysts that are useful in the polymerization of syndiotactic polyolefins, and more particularly syndiotactic polypropylene.

In addition to a newly discovered catalyst, the present invention also provides syndiotactic polypropylene with a new microstructure. It was discovered that the catalyst structure not only affected the formation of a syndiotactic polymer as opposed to an isotactic polymer, but it also appears to affect the type and number of deviations in the chain from the principally repeating units in the polymer. Previously, the catalysts used to produce syndiotactic polypropylene were believed to exercise chain-end control over the polymerization mechanism. These previously known catalysts, such as the ones disclosed by Natta et al in the references cited above, produce predominately syndiotactic polymers having the structure

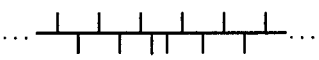

or in NMR nomenclature ...rrrrmrrrrr.... The NMR analysis for this structure of syndiotactic polypropylene is shown in Zambelli, et al., Macromolecules, Vol. 13, pp 267–270 (1980). Zambelli's analysis shows the predominance of the single meso dyad over any other deviation in the chain. It was discovered, however, that the catalysts of the present invention produce a polymer with a different microstructure than that previously known and disclosed, and in addition one having a high percentage of racemic dyads in the structure.

SUMMARY OF THE INVENTION

The present invention provides a catalyst and process for preparing syndiotactic polyolefins, and more particulary syndiotactic polypropylene. The catalyst and process produce a polymer with a high syndiotactic index and with a novel syndiotactic microstructure. Further, the invention includes a process for producing syndiotactic polypropylene having a broad molecular weight distribution and a process for tailoring the characteristics of the polymer such as melting point by varying the structure of the catalyst.

The novel catalyst provided by the present invention is a stereorigid metallocene catalyst described by the formula:

wherein each Cp is a cyclopentadienyl or substituted cyclopentadienyl ring; each $R_n$ and $R'_m$ is a hydrocarbyl radical having 1-20 carbon atoms; R" is a structural bridge between the two Cp rings imparting stereorigidity to the Cp rings; Me is a transition metal; and each Q is a hydrocarbyl radical or is a halogen. Further, $R'_m$ is selected so that $(CpR'_m)$ is a sterically different substituted cyclopentadienyl ring than $(CpR_n)$. It was discovered that the use of a metallocene catalyst with sterically different cyclopentadienyl rings produces a predominantly syndiotactic polymer rather than an isotactic polymer.

The present invention further provides a process for producing syndiotactic polyolefins, and particularly, syndiotactic polypropylene, that comprises utilizing at least one of the catalysts described by the above formula and introducing the catalyst into a polymerization reaction zone containing an olefin monomer. In addition, an electron donor compound and/or a cocatalyst such as alumoxane may be introduced into the reaction zone. Further, the catalyst may also be pre-polymerized prior to introducing it into the reaction zone and/or prior to the stabilization of reaction conditions in the reactor.

The present invention also includes a process for producing syndiotactic polyolefins having a broad molecular weight distribution. This process comprises utilizing at least too different catalysts described by the above formula in the process of polymerization.

It was further discovered that the characteristics of the polymer produced by the process of polymerization described herein could be controlled by varying the polymerization temperature or the structure of the catalyst. In particular, it was discovered that a higher polymerization temperature resulted in a syndiotactic polymer with a mixed microstructure. Also, it was discovered that the melting points of the polymer are affected by the reaction temperature, the catalyst-cocatalyst ratio, and the structure of the catalyst. A higher reaction temperature generally produces a less crystalline polymer having a lower melting point. Further, polymer products having different melting points are obtainable by varying the structure of the catalyst.

The present invention further includes a process for preparing a bridged metallocene catalyst comprising contacting a cyclopentadiene or substituted cyclopentadiene with fulvene or a substituted fulvene under reaction conditions sufficient to produce a bridged dicyclopentadiene or substituted dicyclopentadiene. The process further comprises contacting the bridged dicyclopentadiene with a metal compound of the formula $MeQ_k$ as defined above under reaction conditions sufficient to complex the bridged dicyclopentadiene to produce a bridge metallocene.

DETAILED DESCRIPTION

Figure 1:
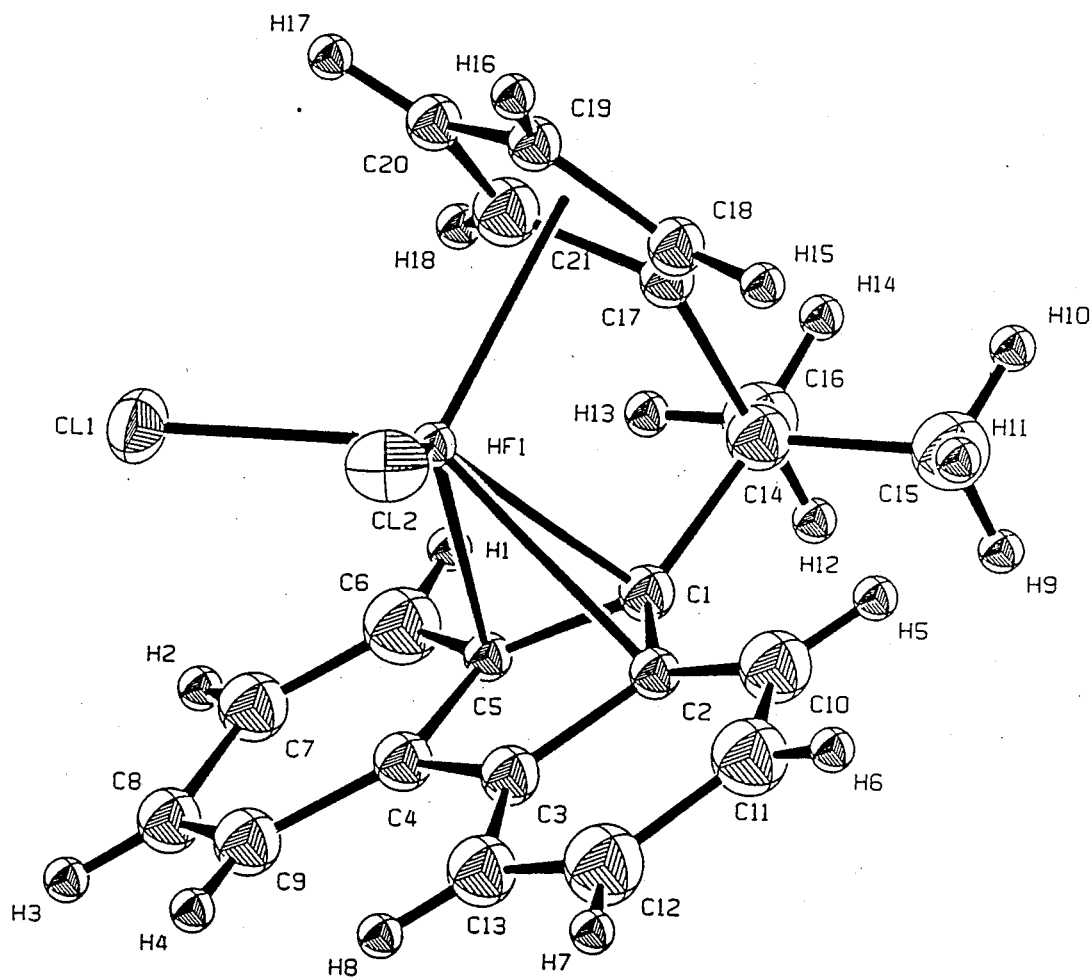
FIG. 1 is an illustration of the structure of a preferred catalyst of the present invention and specifically shows iso-propyl(cyclopentadienyl) (fluorenyl)hafnium dichloride.

The present invention provides a catalyst and process for the production of syndiotactic polyolefins, particularly polypropylene. Not only do the catalysts of the present invention produce syndiotactic polypropylene, but they also produce a polymer with a novel microstructure.

When propylene or other alpha-olefins are polymerized using a catalyst consisting of a transition metal compound, the polymer product typically comprises a mixture of amorphous atactic and crystalline xylene insoluble fractions. The crystalline fraction may contain either isotactic or syndiotactic polymer, or a mixture of both. Highly iso-specific metallocene catalysts are disclosed in copending U.S. Application Ser. Nos. 034,472; 096,075; and 095,755. In contrast to the catalysts disclosed in those applications, the catalysts of the present invention are syndio-specific and produce a polymer with a high syndiotactic index. It was discovered that syndiotactic polymers generally have lower heats of crystallization than the corresponding isotactic polymers. In addition, for the same number of imperfections in the polymer chain, syndiotactic polymers have a higher melting point that isotactic polymers.

The metallocene catalysts of the present invention may be described by the formula $R''(CpR_n)(CpR'_m)MeQ_k$ wherein each Cp is a cyclopentadienyl or substituted cyclopentadienyl ring; $R_n$ and $R'_m$ are hydrocarbyl radicals having 1-20 carbon atoms, each $R_n$ may be the same or different, and each $R'_m$ also may be the same or different; R" is a structural bridge between the two Cp rings imparting stereorigidity to the Cp rings within the catalyst, and R" is preferably selected from the group consisting of an alkyl radical having 1-4 carbon atoms or a hydrocarbyl radical containing silicon, germanium, phosphorus, nitrogen, boron, or aluminum; Me is a group 4b, 5b, or 6b metal from the Periodic Table of Elements; each Q is a hydrocarbyl radical having 1-20 carbon atoms or is a halogen; $0 \leq k \leq 3$; $0 \leq n \leq 4$; and $1 \leq m \leq 4$. In order to be syndiospecific, it was discovered that the Cp rings in the metallocene catalysts must be substituted in a substantially different manner so that there is a steric difference between the two Cp rings, and therefore, $R'_m$ is selected such that $(CpR'_m)$ is a substantially different substituted ring than (CpR$_n$). In order to produce a syndiotactic polymer, the characteristics of the groups substituted directly on the cyclopentadienyl rings seem to be important. Thus, by "steric difference" or "sterically different" as used herein, it is intended to imply a difference between the steric characteristics of the Cp rings that controls the approach of each successive monomer unit that is added to the polymer chain. The steric difference between the Cp rings acts to block the approaching monomer from a random approach and controls the approach such that the monomer is added to the polymer chain in the syndiotactic configuration.

Without intending to limit the scope of the present invention as indicated by the claims, it is believed that in the polymerization reaction both the catalyst and the approaching monomer units isomerize with each monomer addition to the polymer chain. This isomerization of the monomer which is controlled by the steric blockage of the differently substituted Cp rings results in the alternating configuration characteristic of syndiotactic polymers and is in contrast to the chain-end control of the catalysts disclosed by Natta et al. The different reaction mechanism also results in a different structure for the polymer.

In a preferred catalyst of the present invention, Me is titanium, zirconium or hafnium; Q is preferably a halogen, and it is most preferably chlorine; and k is preferably 2, but it may vary with the valence of the metal atom. Exemplary hydrocarbyl radicals include methyl, ethyl, propyl, isopropyl, butyl, isobutyl, amyl, isoamyl, hexyl, heptyl, octyl, nonyl, decyl, cetyl, phenyl, and the like. Other hydrocarbyl radicals useful in the present catalysts include other alkyl, aryl, alkenyl, alkylaryl or arylalkyl radicals. Further, R$_n$ and R'$_m$ may comprise hydrocarbyl radicals attached to a single carbon atom in the Cp ring as well as radicals that are bonded to two carbon atoms in the ring. FIG. 1 shows the structure of a preferred catalyst isopropyl(fluorenyl) (cyclopentadienyl) hafnium dichloride. The zirconium analogue of the catalyst shown in FIG. 1 is similarly preferred.

The catalyst may be prepared by any method known in the art. The Examples below disclose two methods of preparing the catalyst with the second method being preferred as it produces a more stable and active catalyst. It is important that the catalyst complex be "clean" as usually low molecular weight, amorphous polymer is produced by impure catalysts. Generally, the preparation of the catalyst complex consists of forming and isolating the Cp or substituted Cp ligands which are then reacted with a halogenated metal to form the complex.

The metallocene catalysts of the present invention are useful in many of the polymerization processes known in the art including many of those disclosed for the preparation of isotactic polypropylene. When the catalysts of the present invention are used in these types of processes, the processes produce syndiotactic polymers rather than isotactic polymers. Further examples of polymerization processes useful in the practice of the present invention include those disclosed in U.S. Application Ser. No. 009,712 filed on Feb. 2, 1987 and now U.S. Pat. No. 4,767,735 and U.S. Application Ser No 095,755 filed on Sept. 11, 1987 and now abandoned, the disclosures of which are hereby incorporated herein by reference. These preferred polymerization procedures include the step of prepolymerizing the catalyst and/or precontacting the catalyst with a cocatalyst and an olefin monomer prior to introducing the catalyst into a reaction zone.

Consistent with the prior disclosures of metallocene catalysts for the production of isotactic polymers, the syndio-specific catalysts of the present invention are particularly useful in combination with an aluminum cocatalyst, preferably an alumoxane, an alkyl aluminum, or a mixture thereof. In addition, a complex may be isolated between a metallocene catalyst as described herein and an aluminum cocatalyst in accordance with the teachings of European Patent Publication No. 226,463 published on June 24, 1987 and assigned to Exxon Chemical Patents Inc. with Howard Turner listed as the inventor. As disclosed therein, a metallocene is reacted with an excess of alumoxane in the presence of a suitable solvent. A complex of the metallocene and alumoxane may be isolated and used as a catalyst in the present invention.

The alumoxanes useful in combination with the catalysts of the present invention, either in the polymerization reaction or in forming the complex disclosed in Turner, may be represented by the general formula (R—Al—0—) in the cyclic form and R(R—Al—0)$_n$—ALR2 in the linear form wherein R is an alkyl group with one to five carbon atoms and n is an integer from 1 to about 20. Most preferably, R is a methyl group. The alumoxanes can be prepared by various methods known in the art. Preferably, they are prepared by contacting water with a solution of trialkyl aluminum, such as, trimethyl aluminum, in a suitable solvent such as benzene. Another preferred method includes the preparation of alumoxane in the presence of a hydrated copper sulfate as described in U.S. Pat. No. 4,404,344 the disclosure of which is hereby incorporated by reference. This method comprises treating a dilute solution of trimethyl aluminum in toluene with copper sulfate. The preparation of other aluminum cocatalysts useful in the present invention may be prepared by methods known to those skilled in the art.

The Examples given below illustrate the present invention and its various advantages and benefits in more detail. Two different synthesis procedures, designated as A and B, are described for both zirconium and hafnium metallocene catalysts. The synthesis procedures in both methods were performed under an inert gas atmosphere using a Vacuum Atmospheres glovebox or Schlenk techniques. The synthesis process generally comprises the steps of (1) preparing the halogenated or alkylated metal compound, (2) preparing the ligand, (3) synthesizing the complex, and (4) purifying the complex. The synthesis of the bridged, substituted dicyclopentadienyl ligand was accomplished by contacting fulvene or a substituted fulvene with a cyclopentadienyl or substituted cyclopentadienyl under reaction conditions sufficient to produce a bridged dicyclopentadiene or substituted dicyclopentadiene. As known in the art, fulvene is Cp=C in which a carbon atom is bound by a double bond to a cyclopentadienyl ring. Substituted fulvene as used herein is intended to mean (CpR$_a$)=CR'$_b$ wherein fulvene is substituted either on the Cp ring or at the terminal carbon atom or both. R$_a$ and R$_b$' are hydrocarbyl radicals, with each R$_a$ and R$_b$' being the same or different, and $0 \leq a \leq 4$ and $0 \leq b \leq 2$. The other three steps of the synthesis may be performed as shown below or other methods known in the art. The general catalyst formula for the catalyst produced by these methods is iso-propyl(fluorenyl)(cyclopentadienyl) MeCl$_2$ wherein Me is either zirconium or hafnium depending on the example. FIG. 1 shows the structure of the hafnium catalyst, and the zirconium catalyst has essentially the same structure with Zr positioned in place of the Hf atom.

Preparation of the Catalyst

Method A

In Method A, the halogenated metal compound was prepared using tetrahydrofuran ("THF") as a solvent resulting in THF bound in with the final catalyst complex. Specifically, MeCl$_4$THF was prepared as described in Manzer, L., *Inorg. Synth.*, 21, 135–36 (1982). In the Examples below, Me is zirconium and hafnium, but it may also include titanium or other transition metals.

The substituted dicyclopentadienyl ligand may be prepared using various processes known in the art depending upon the selection of the specific bridge or ring substituents. In the preferred embodiments shown in the Examples below, the ligand is 2,2-isopropyl(fluorene)-cyclopentadiene. To prepare this ligand, 44 gms (0.25 mol) of fluorene were dissolved in 350 ml THF in a round bottom flask equipped with a side arm and dropping funnel. Contained within the funnel were 0.25 mol of methyl lithium (CH$_3$Li) in ether (1.4 M). The CH$_3$Li was added dropwise to the fluorene solution and the deep orange-red solution was stirred for several hours. After gas evolution had ceased, the solution was cooled to −78° C. and 100 ml of THF containing 26.5 gms (0.25 mol) of 6,6-dimethylfulvene was added dropwise to the solution. The red solution was gradually warmed to room temperature and stirred overnight. The solution was treated with 200 ml of water and stirred for ten minutes. The organic fraction of the solution was extracted several times with 100 ml portions of diethylether, and the combined organic phases were dried over magnesium sulfate. Removal of the ether from the organic phases left a yellow solid which was dissolved in 500 ml of chloroform and recrystallized by addition of excess methanol at 2° C. to yield a white powder.

The elemental analysis of the ligand showed carbon to be 91.8% by weight of the compound and hydrogen to be 7.4% by weight. This corresponds to the weight percentages for C$_{21}$H$_{20}$, 92.6% carbon and 7.4% hydrogen. The NMR spectrum for the ligand establishes the structure to include one cyclopentadienyl ring attached by an isopropyl bridge to a second cyclopentadienyl ring that is substituted to form a fluorenyl radical.

A syndio-specific catalyst complex was synthesized using the ligand and the metal tetrachloride-THF complex. The catalyst was formed by adding 0.05 mol of N-butyl lithium hexane (1.6M) dropwise to a 100 ml THF solution containing 6.8 gms (0.025 mol) of the Cp ligand described above. The solution was stirred at 35° C. for twelve hours after which 9.4 gms (0.025 mol) of ZrCl$_4$-2THF contained in 200 ml of THF were rapidly cannulated together with the ligand solution into a 500 ml round bottom flask with vigorous stirring. The deep orange-red solution was stirred for twelve hours under reflux. A mixture of LiCl red solid were isolated by removing the solvents under vacuum.

Catalyst complexes produced in accordance with Method A are noted to be somewhat impure and extremely air and moisture sensitive. As a result, in the Examples below, Method A catalysts were purified using one or more of the following purification procedures:

1. Extraction with pentane. Trace quantities of a yellow impurity contained in the solid red catalyst complex were repeatedly extracted with pentane until the pentane became colorless.

2. Fractional recrystallization. The red complex was separated from the white LiCl by dissolving it in 100 ml of toluene, filtering it through a fine porosity sintered glass frit, and forming a saturated solution by adding pentane. The red zirconium complex was isolated using crystallization at −20° C.

3. Chromotography on bio-beads. 50 gms of bio-beads SM-2 (20–50 mesh spherical, macroreticular styrene-divinylbenzene copolymer from Bio-Rad laboratories) were dried under vacuum at 70° C. for 48 hours in a 30 × 1.5 centimeter column. The beads were then equilibrated with toluene for several hours. A concentrated solution of the red catalyst complex in toluene was eluted down the column with 150–200 ml of toluene. The complex was recovered by evaporating the toluene under vacuum.

Catalyst Synthesis Procedure

Method B

As an alternative synthesis procedure, Method B provides catalysts that are more air stable, more active, and produce a higher percentage of syndiotactic polypropylene. In this process, methylene chloride is used as a non-coordinating solvent. The process described below uses hafnium as the transition metal, but the procedure is adaptable for use with zirconium, titanium or other transition metals. The substituted dicyclopentadienyl ligand was synthesized in THF in the same manner as described in Method A above. The red dilithio salt of the ligand (0.025 mol) was isolated as disclosed in Method A by removing the solvents under vacuum and by washing with pentane. The isolated red dilithio salt was dissolved in 125 ml of cold methylene chloride and an equivalent amount (0.025 mol) of HfCl$_4$ was separately slurried in 125 ml of methylene chloride at −78° C. The HfCl$_4$ slurry was rapidly cannulated into the flask containing the ligand solution. The mixture was stirred for two hours at −78° C., allowed to warm slowly to 25° C. and stirred for an additional 12 hours. An insoluble white salt (LiCl) was filtered off. A moderately air sensitive, yellow powder was obtained by cooling the brown/yellow methylene chloride solution to −20° C. for 12 hours and cannulating away the supernatant. The bright yellow product was washed on the sintered glass filter by repeatedly filtering off cold supernatant that had been cannulated back over it. The catalyst complex was isolated by pumping off the solvents using a vacuum, and it was stored under dry, deoxygenated argon. The process yielded 5.5 gms of catalyst complex.

The elemental analysis of the hafnium catalyst complex prepared using Method B showed that the catalyst consisted of 48.79% by weight of carbon, 3.4% hydrogen, 15.14% chlorine and 33.2% hafnium. These percentages compare with the theoretical analysis for C$_{21}$H$_{18}$HfCl$_2$ which is 48.39% carbon, 3.45% hydrogen, 13.55% chlorine and 34.11% hafnium. Similarly, zirconium catalysts produced using Method B show elemental analysis close to the expected or theoretical values. Further, some of the hafnium complexes illustrated in the Examples below were made using 96% pure HfCl$_4$ which also contains about 4% ZrCl$_4$. Still other catalyst samples were made using 99.99% pure HfCl₄. Differences can be seen in the molecular weight distributions of the polymers produced with the pure Hf catalyst compared with the polymers produced using the catalysts which contain a small percentage of zirconium. The mixed catalyst produces a polymer with a broader molecular weight distribution than that produced by a pure catalyst system.

The Examples below illustrate the present invention and its various advantages in more detail. The results of the polymerization process and the analysis of the polymer are shown in Table 1 for Examples 1-17 and Table 2 for Examples 18-33.

EXAMPLE 1

The polymerization of propylene was carried out using 0.16 mg of isopropyl(cyclopentadienyl)(florenyl) zirconium dichloride produced in accordance with Method A described above. The catalyst was purified using fractional recrystallization. The catalyst was precontacted for 20 minutes with a toluene solution containing 10.7% by weight of methylalumoxane (MAO) with an average molecular weight of about 1300. The alumoxane serves as a co-catalyst in the polymerization reaction. Ten cc of the MAO solution was used in the polymerization. The catalyst and co-catalyst solution was then added to a Zipperclave reactor at room temperature followed by the addition of 1.2 liters of liquid propylene. The reactor contents were then heated to the polymerization temperature, T as shown in Tables 1 and 2, of 20° C. in less than about 5 minutes. During this time, prepolymerization of the catalyst occurred. The polymerization reaction was allowed to run for 60 minutes during which time the reactor was maintained at the polymerization temperature. The polymerization was terminated by rapidly venting the monomer. The reactor contents were washed with 50% methanol in dilute HCl solution and dried in vacuo. The polymerization yielded 14 gms of polypropylene "as polymerized", i.e., without any further isolations or purification.

Analysis of Polymer

The polymer was analyzed to determine the melting point Tm, the heat of crystallization Hc, the molecular weights Mp, Mw, and $M_n$, the percent of xylene insolubles XI, and the syndiotactic index S.I. Unless otherwise noted, the analyses were performed on the xylene insoluble fraction of the polymer which includes the syndiotactic fraction and any isotactic polymer produced. The atactic polymer was removed by dissolving the polymer product in hot xylene, cooling the solution to 0° C. and precipitating out the xylene insoluble fraction. Successive recrystallizations performed in this manner result in removing essentially all atactic polymer from the xylene insoluble fraction.

The melting points, Tm, were derived using Differential Scanning Calorimetry (DSC) data as known in the art. The melting points, Tm1 and Tm2 listed in Tables 1 and 2 are not true equilibrium melting points but are DCS peak temperatures. In polypropylene, it is not unusual to get an upper and a lower peak temperature, i.e., two peaks, and both melting points are reported in Tables 1 and 2 with the lower melting point reported as Tm1 and the higher point as Tm2. True equilibrium melting points obtained over a period of several hours would most likely be several degrees higher than the DSC lower peak melting points. As is known in the art, the melting points for polypropylene are determined by the crystallinity of the xylene insoluble fraction of the polymer. This has been shown to be true by running the DSC melting points before and after removal of the xylene soluble or atactic form of the polymer. The results showed only a difference of 1-2° C. in the melting points after most of the atactic polymer was removed. As shown in Table 1, the melting points were determined to be 145° C. and 150° C. for the polymer produced in Example 1. DSC data was also used to determine the heat of crystallization, −Hc as shown in Tables 1 and 2, measured in joules per gram J/g. The melting points and −Hc were determined on the "as polymerized" sample before the atactic polymer was removed.

The molecular weights of the polymer were calculated using Gel Permeation Chromotography (GPC) analysis done on a Waters 150° C. instrument with a column of Jordi gel and an ultra-high molecular weight mixed bed. The solvent was trichlorobenzene and the operating temperature was 140° C. From GPC, $M_p$ which is the peak molecular weight, $M_n$ which is the number average molecular weight and $M_w$ which is the weight average molecular weight were derived for the xylene insolube fraction of the polymer produced. The molecular weight distribution, MWD, is commonly measured as $M_w$ divided by $M_n$. The values determined for this sample are shown in Table 1. GPC analysis was also used to determine the syndiotactic index, S.I.%, shown in Tables 1 and 2. The syndiotactic index is a measure of the percentage of the syndiotactic structure produced in the polymerization reaction and was determined from the molecular weight data on the samples "as polymerized."

Figure 2:
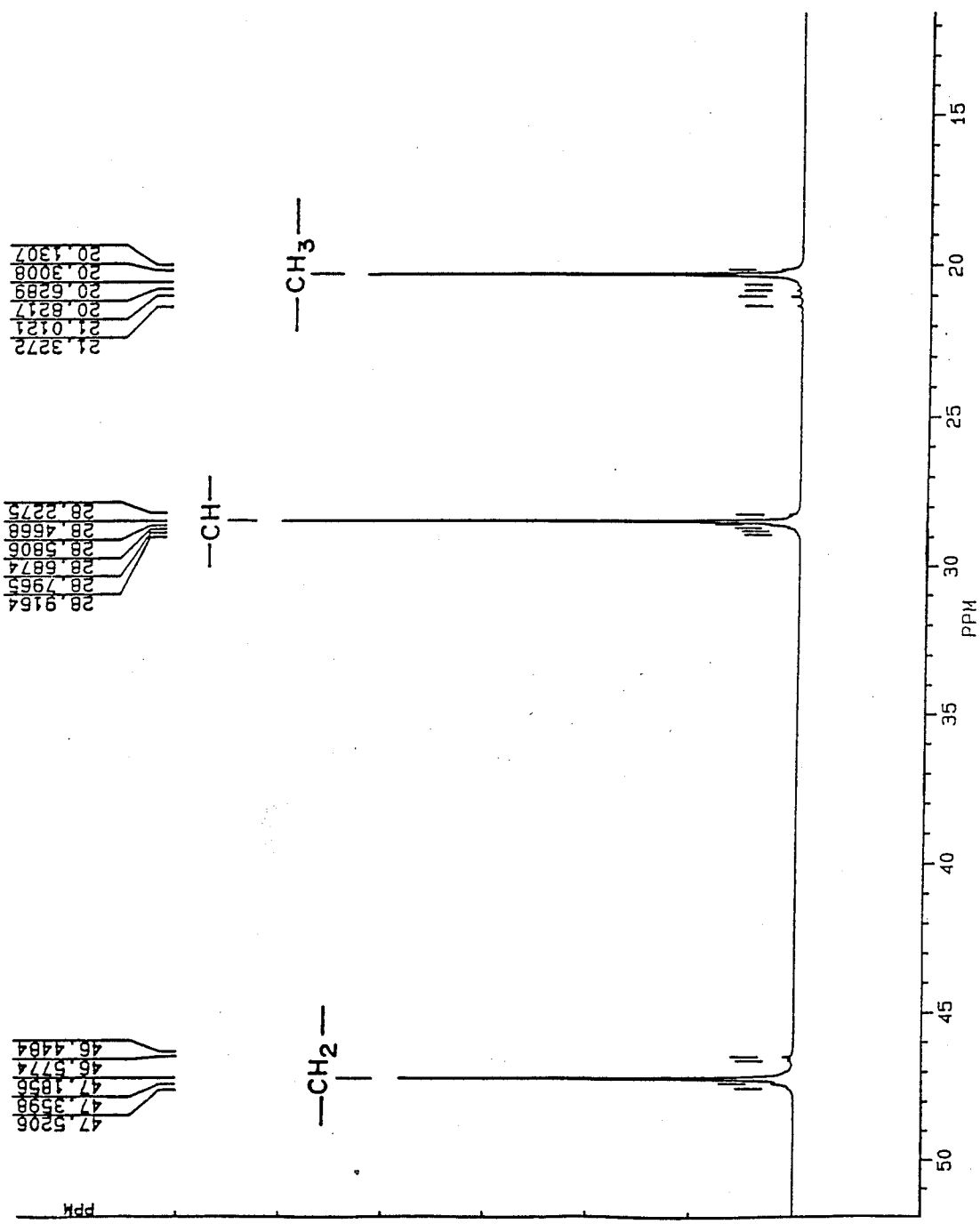
FIG. 2 is an NMR spectra for the polymer produced in Example 1 using iso-propyl(cyclopentadienyl) (fluorenyl) zirconium dichloride. The polymer was recrystallized once from xylene.

NMR analysis was used to determine the microstructure of the polymer. A sample of the polymer produced above was dissolved in a 20% solution of 1,2, 4-trichlorobenzene/d₆-benzene and run on a Bruker AM 300 WB spectrometer using the inverse gate broad band decoupling method. The experimental conditions were: transmitter frequency 75.47 MHz; decoupler frequency 300.3 MHz; pulse repetition time 12 seconds; acquisition time 1.38 seconds; pulse angle 90° (11.5 microseconds pulse width); memory size 74K points; spectral window, 12195 Hz. Seven thousand transients were accumulated, and the probe temperature was set at 133° C. The NMR spectrum for the polymer produced and recrystallized from xylene one time is shown in FIG. 2. The calculated and observed values for the spectra are shown in Table 3 with Example 1 representing the data for the sample recrystallized once from xylene and Example 1-A representing the data for the sample recrystallized three times from xylene. The calculated values were derived using the Bernoullian probability equations as disclosed in Inoue Y., et al, *Polymer*, Vol. 25, page 1640 (1984) and as known in the art.

The results show that in the sample recrystallized once from xylene the percentage of racemic dyads (r) is 95%. For the sample recrystallized three times from xylene the percentage of r dyads is 98% indicating a polymer that consists of 2% or less of the meso (m) dyad. Further, the NMR spectrum shows that the meso dyads occur predominately in pairs, i.e., mm triads, as opposed to the previously known single m dyad structure in the chain. Thus, the catalysts of the present invention produce a polymer product with a novel microstructure from that previously known.

EXAMPLE 2

The procedures of Example 1 were repeated except that 500 ml of toluene was used as a co-solvent in the polymerization reaction. Further, one gram of MAO was used in the polymerization, and the reaction temperature was 50° C. Fifteen grams of oil were obtained along with the polymer product. The polymer was analyzed in accordance with the procedures given above and the results are shown in Table 1.

EXAMPLE 3

The procedures of Example 2 were repeated except that hafnium was used as the transition metal in the catalyst. The other reaction conditions were as shown in Table 1, and the analyzed properties of the resulting polymer are also shown in Table 1.

Figure 4:
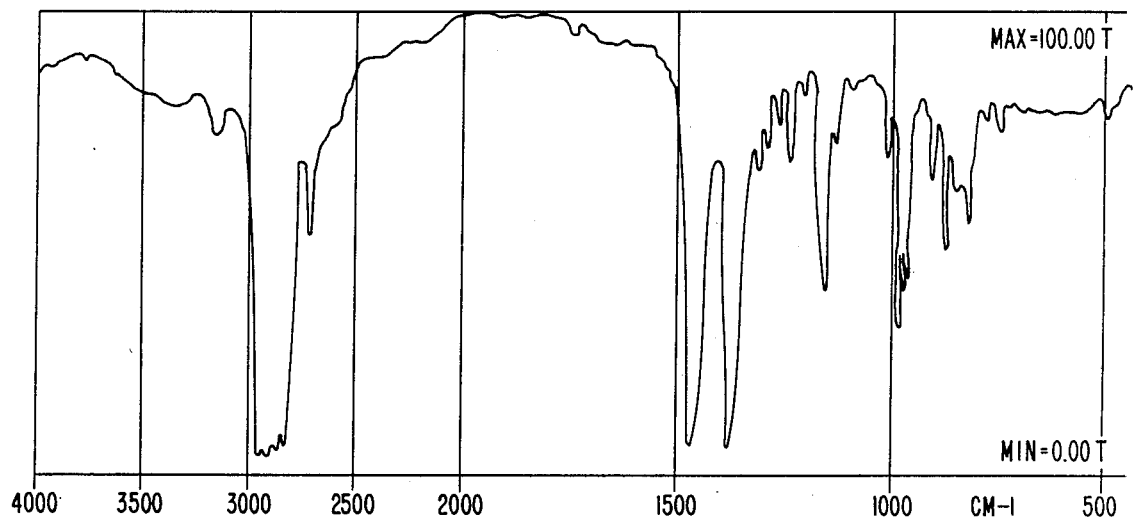
Figure 4:
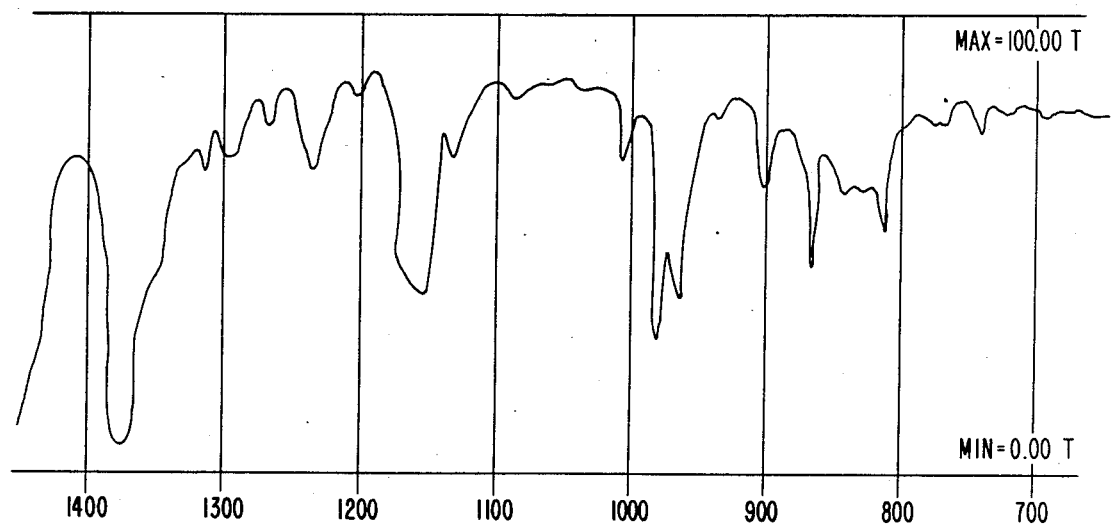

FIGS. 4 and 5 show the IR spectra for the polymer produced in Examples 7 and 8 respectively. The characteristic bands at 977 and 962 cm$^{-1}$ for syndiotactic polypropylene are readily visible. The presence of these bands reaffirm the syndiotactic structure of the polymer. The corresponding bands for isotactic polypropylene are 995 and 974 respectively.

EXAMPLES 4 THROUGH 8

The procedures of Example 1 were repeated except for the differing reaction conditions as shown in Table 1. In addition, Example 4 used chromotography as the purification procedure and Example 5 utilized no purification procedure. The results of the polymerization and the analysis of the polymer are shown in Table 1.

Figure 3:
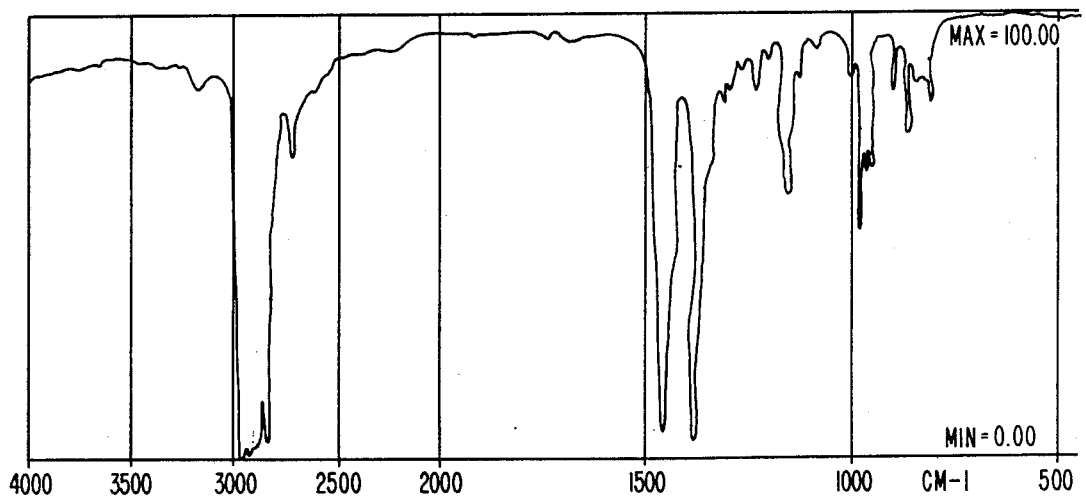
FIGS. 3 and 4 are IR spectra for the polymers produced in Examples 7 and 8 respectively with the polymer being recrystallized three times from xylene.
Figure 3:
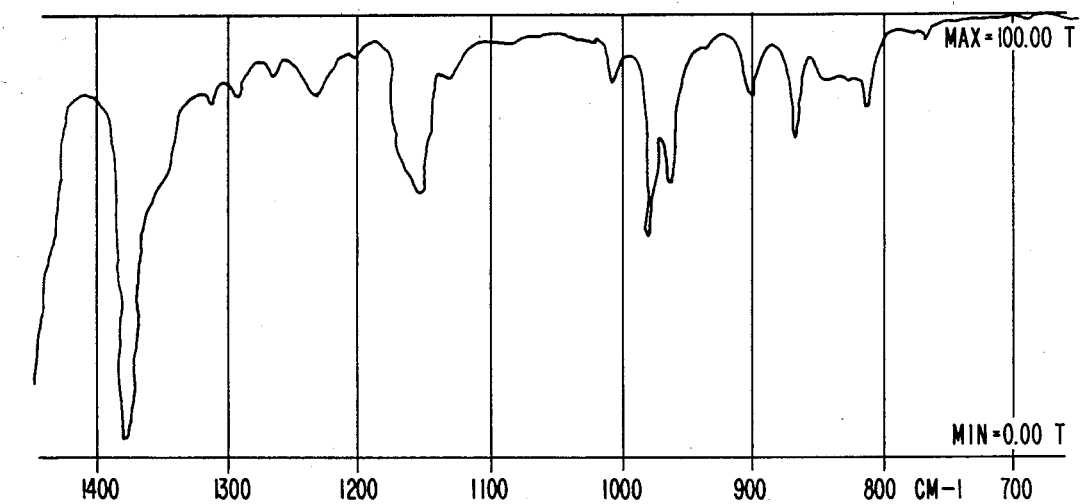

FIGS. 3 and 4 show the IR spectra for the polymers produced in Examples 7 and 8 respectively with the polymer recrystallized three times.

EXAMPLES 9–16

The procedures of Example 1 were repeated except for the changes in the amounts of catalyst and cocatalyst as indicated in Table 1. Further, the catalysts in Examples 9–13 and 15 were purified using both extraction with pentane and fractional recrystallization. Example 14 used extraction with pentane and chromotography as the purification procedures. Example 16 did not use any purification procedure.

EXAMPLE 17

The procedures of Example 1 were repeated except that hafnium was used as the transition metal for the catalyst. The other reaction conditions were as shown in Table 1. The catalyst was purified using extraction with pentane and fractional recrystallization. The results of the polymerization are shown in Table 1.

EXAMPLES 18 AND 19

A hafnium metallocene catalyst was synthesized using Method B as described above and using the 95% pure HfCl$_4$ that contained about 4% ZrCl$_4$. The polymerization was carried out using the polymerization procedures of Example 1 under the conditions shown in Table 2. The polymers were analyzed in accordance with the procedures set forth in Example 1 and the results are shown in Table 2.

EXAMPLES 20–31

A zirconium metallocene catalyst was prepared using the synthesis procedures of Method B, and the polymerization of propylene was carried out under the conditions shown for each Example in Table 2. The polymer products were analyzed in accordance with the procedures of Example 1 and the results are given in Table 2. It should be noted that for Examples 20–22, the syndiotactic index, S.I., was determined for the xylene insoluble fraction. The syndiotactic index for these fractions were nearly 100%. The observed (obsd.) NMR spectra data for Examples 20 and 22 are shown in Table 4. The data given for Examples 20 and 22 was collected from the polymers produced in Examples 20 and 22 respectively and recrystallized once from xylene. Example 22-A is the polymer of Example 22 that is recrystallized three times from xylene.

EXAMPLES 32–33

A hafnium metallocene catalyst was prepared using the synthesis procedures of Method B. The catalyst for Example 32 was prepared using the 99% pure HfCl$_4$ while the catalyst in Example 33 was prepared from the 95% pure HfCl$_4$ that contained about 4% ZrCl$_4$. The polymerization was carried out in accordance with the procedures of Example 1 under the conditions shown for Examples 32 and 33 in Table 2. The results of the analysis of the polymer produced in these Examples are also shown in Table 2. The NMR data for Example 33 is shown in Table 4 with the sample as recrystallized once from xylene (Ex. 33) and three times from xylene (Ex. 33A).

The data shown in Tables 1–4 and in FIGS. 2 and 3 show that the catalysts of the present invention produce a predominantly syndiotactic polymer that has high crystallinity and a novel microstructure. Particularly, the NMR data shown in Tables 3 and 4 establish that the xylene insoluble fraction consists of a very high percentage of syndiotactic polymer with very little, if any, isotactic polymer being produced. Further, the syndiotactic polymer contains a high percentage of "r" groups and "rrrr" pentads indicating that there is only a small percentage of deviations from the "...rrrr..." structure in the polymer chain. The deviations that do exist are predominantly of the "mm" type. Indeed, the results for Ex. 1-A in Table 3 show that the only deviation in the chain is of the "mm" type. The other NMR samples show the predominance of the "mm " deviation over the "m" deviation. Thus, a novel microstructure for syndiotactic polypropylene has been discovered.

The data in Tables 1 and 2 shows the high crystallinity of the polymer product. The relatively high melting points, TM1 and TM2, and the relatively high heats of crystallization, −Hc, indicate that the polymers are highly crystalline. The data further indicates a corelation between the polymerization reaction temperature, T, and the melting points, molecular weights and the heats of crystallization of the polymer. As the reaction temperature increases, all three of these properties decrease. There also seems to be a range of temperature within which the yield of polymer is maximized. This temperature range will vary with the type of catalyst used but is typically 50–70° C. The concentration of methylalumoxane (MAO) also appears to affect the polymer yield. The data indicates that to a point, the greater the concentration of MAO, the higher the yield of polymer. The concentration of MAO also seems to have some effect on the amount of atactic polymer produced. MAO appears to act like a scavenger for impurities and tends to reduce the amount of atactic polymer produced.

The data further indicates a difference between the zirconium catalysts and the hafnium catalysts of the present invention. The polymers produced with the hafnium catalysts tend to be less crystalline and have lower melting points than the polymers produced with the zirconium catalysts. The data in Table 4 also shows that the hafnium catalyst produces a higher percentage of isotactic blocks in the polymer chain as reflected by the presents of the isotactic pentad mmmm.

Examples 18, 19 and 33 show the ability to achieve a broader molecular weight distribution, MWD=Mw/Mn, by use of a mixture of two or more of the catalysts described by the present invention. The catalysts in these Examples were prepared using HfCl₄ that contained about 4% ZrCl₄. The MWD of the polymer in these Examples is significantly higher than the MWD of the polymer produced by an essentially pure hafnium catalyst —see Example 32. Thus, a mixture of two different catalysts can be used to produce a polymer with a broad MWD.

It should be further understood that the syndiospecific catalysts of the present invention are not limited to the specific structures recited in the Examples, but rather, include catalysts described by the general formula given herein in which one Cp ring is substituted in a substantially different manner so as to be sterically different. In the Examples above, the rings included an unsubstituted Cp ring and a Cp ring substituted to form a fluorenyl radical, but similar results are obtainable through the use of other ligands consisting of bridged Cp rings in which one of the Cp rings is substituted in a substantially different manner from the other Cp ring, e.g., an indenyl radical and a Cp ring, a tetramethyl substituted Cp ring and a Cp ring, a dialkyl substituted Cp ring and a monoalkyl substituted ring, etc.

From the detailed description of the invention just given, it is apparent that the invention provides a catalyst and a process for preparing syndiotactic polyolefins. Having described but a few embodiments, it will be apparent to one skilled in the art that various modifications and adaptations may be made to the catalysts and processes as described without departing from the scope of the present invention.

TABLE 1

| Example | Metal | Catalyst (mg) | MAO (cc) | T °C. | Yield (g) | Tm 1° C. | Tm 2° C. | -Hc J/g | Mp/1000 | Mw/Mn | S.I. % |
|---|---|---|---|---|---|---|---|---|---|---|---|
| | | | | Method A | | | | | | | |
| 1 | Zr | 10.0 | 10.0 | 20 | 14 | 145 | 150 | 43 | 118 | 2.5 | 62 |
| 2 | Zr | 10.3 | 1 g | 50 | 26 | 129 | 137 | 45 | 57 | 1.9 | 68 |
| 3 | Hf | 10.3 | 1 g | 50 | 12 | | 104 | 17 | 1222 | | 46 |
| 4 | Zr | 5.0 | 10.0 | 50 | 130 | 132 | 138 | 37 | 61 | | 87 |
| 5 | Zr | 5.1 | 10.0 | 50 | 83 | 131 | 138 | 38 | 62 | | 84 |
| 6 | Zr | 5.0 | 0.3 g | 70 | 22 | 115 | 127 | 34 | 71 | | 83 |
| 7 | Zr | 5.1 | 5.0 | 50 | 68 | 131 | 140 | 37 | 60 | | 38 |
| 8 | Zr | 5.1 | 10.0 | 50 | 110 | 132 | 140 | 38 | 60 | | 42 |
| 9 | Zr | 5.1 | 1.0 | 50 | 14 | 114 | 126 | 21 | 58 | | 24 |
| 10 | Zr | 5.0 | 2.5 | 50 | 34 | 111 | 122 | 14 | 60 | | 23 |
| 11 | Zr | 5.1 | 5.0 | 50 | 68 | 119 | 130 | 21 | 60 | | 38 |
| 12 | Zr | 5.0 | 10.0 | 50 | 78 | 128 | 137 | 32 | 64 | | 65 |
| 13 | Zr | 5.0 | 1.0 | 50 | 83 | 121 | 132 | 22 | 59 | | 42 |
| 14 | Zr | 2.6 | 10.0 | 50 | 85 | 134 | 140 | 40 | 62 | | 89 |
| 15 | Zr | 5.1 | 10.0 | 50 | 110 | 125 | 134 | 29 | 60 | | 42 |
| 16 | Zr | 5.1 | 10.0 | 50 | 115 | 131 | 138 | 38 | 62 | | 84 |
| 17 | Hf | 10.3 | 1 g | 80 | 55 | 89 | 108 | | 223 | | 52 |

TABLE 2

| Example | Metal | Catalyst (mg) | MAO (cc) | T °C. | Yield (g) | Tm 1° C. | Tm 2° C. | -Hc J/g | Mw/1000 | Mw/Mn | S.I. % |
|---|---|---|---|---|---|---|---|---|---|---|---|
| | | | | METHOD B | | | | | | | |
| 18 | Hf | 10.0 | 10 | 50 | 58 | 116 | 125 | 24 | 644 | 5.4 | |
| 19 | Hf | 5.0 | 10 | 50 | 60 | 117 | 124 | 24 | 774 | 4.8 | |
| 20 | Zr | 0.6 | 10 | 50 | 162 | 134 | 140 | 40 | 69 | 1.8 | 95 |
| 21 | Zr | 1.5 | 10 | 29 | 49 | 142 | 146 | 45 | 106 | 1.9 | 95 |
| 22 | Zr | 0.6 | 10 | 70 | 119 | | 134 | 39 | 54 | 2.0 | 95 |
| 23 | Zr | 0.2 | 10 | 50 | 27 | 135 | 140 | 39 | 69 | 1.9 | |
| 24 | Zr | 0.6 | 10 | 50 | 162 | 134 | 140 | 40 | 69 | 1.8 | |
| 25 | Zr | 0.6 | 10 | 25 | 26 | | 145 | 44 | 133 | 1.9 | |
| 26 | Zr | 0.6 | 10 | 70 | 119 | | 134 | 39 | 54 | 2.0 | |
| 27 | Zr | 1.5 | 10 | 29 | 49 | 142 | 146 | 45 | 106 | 1.9 | |
| 28 | Zr | 2.5 | 10 | 50 | 141 | 135 | 141 | 40 | 70 | 1.9 | |
| 29 | Zr | 5.0 | 10 | 28 | 152 | 128 | 137 | 43 | 88 | 2.1 | |
| 30 | Zr | 0.5 | 10 | 60 | 185 | 128 | 137 | 37 | 52 | 1.8 | |
| 31 | Zr | 0.5 | 5 | 70 | 158 | 120 | 134 | 36 | 55 | 2.4 | |
| 32 | Hf | 2.5 | 10 | 70 | 96 | 103 | | 19 | 474 | 2.6 | |
| 33 | Hf | 10.0 | 10 | 50 | 27 | 114 | | 26 | 777 | 5.3 | |

TABLE 3

| | Ex. 1 | | Ex. 1A | |
|---|---|---|---|---|
| | obsd. % | calc. % | obsd. % | calc. % |
| % r | 95 | 95 | 98 | 98 |
| mmmm | 0.3 | 0.2 | 0 | 0 |
| mmmr | 0.3 | 0.6 | 0 | 0 |
| rmmr | 1.5 | 1.4 | 1.3 | 1.0 |
| mmrr | 2.4 | 2.9 | 1.9 | 2.1 |
| rmmr + mmrm | 1.5 | 1.6 | 0 | 0 |
| mrmr | 1.6 | 0.8 | 0 | 0 |
| rrrr | 88.0 | 89.1 | 94.7 | 94.7 |
| mrrr | 3.9 | 3.1 | 2.2 | 2.1 |
| mrrm | 0.4 | 0.4 | 0 | 0 |
| dw | | 0.2 | | 0.1 |

TABLE 4

| | EX. 20 obsd. % | EX. 22 obsd. % | EX. 22-A obsd. % | EX. 33 obsd. % | EX. 33-A obsd. % |
|---|---|---|---|---|---|
| mmmm | 0 | 0.77 | 0.51 | 2.34 | 2.04 |
| mmmr | 0.23 | 0.45 | 0.31 | 0.73 | 0.76 |
| rmmr | 1.67 | 1.82 | 1.81 | 2.72 | 2.96 |
| mmrr | 3.58 | 4.25 | 4.06 | 5.72 | 6.44 |
| mrmm + rmrr | 2.27 | 3.23 | 3.57 | 2.87 | 3.12 |
| mrmr | 1.51 | 2.06 | 1.70 | 1.37 | 1.53 |
| rrrr | 82.71 | 77.58 | 78.12 | 75.7 | 74.55 |
| mrrr | 6.45 | 7.75 | 9.02 | 7.4 | 8.01 |
| mrrm | 0.68 | 0.73 | 0.93 | 1.08 | 0.55 |

We claim:

1. A metallocene catalyst for use in preparing syndiotactic polyolefins, said catalyst described by the formula $R''(CpR_n)(CpR'_m)MeQ_k$ wherein each Cp is a cyclopentadienyl or substituted cyclopentadienyl ring; each $R_n$ is the same or different and is a hydrocarbyl radical having 1-20 carbon atoms; each $R'_m$ is the same or different and is a hydrocarbyl radical having 1-20 carbon atoms; R'' is a structural bridge between the Cp rings imparting stereorigidity to the catalyst; Me is a group 4b, 5b, or 6b metal from the Periodic Table of Elements; each Q is a hydrocarbyl radical having 1-20 carbon atoms or is a halogen; $0 \leq k \leq 3$; $0 \leq n \leq 4$; $1 \leq m \leq 4$; and wherein $R'_m$ is selected such that $(CpR'_m)$ is a sterically different ring than $(CpR_n)$.

2. The catalyst of claim 1 wherein $R'_m$ is selected such that $(CpR'_m)$ forms a fluorenyl or indenyl radical.

3. The catalyst of claim 1 wherein Me is titanium, zirconium or hafnium.

4. The catalyst of claim 1 wherein R'' is selected from the group consisting of an alkylene radical having 1-4 carbon atoms, a silicon hydrocarbyl radical, a germanium hydrocarbyl radical, a phosphorus hydrocarbyl radical, a nitrogen hydrocarbyl radical, a boron hydrocarbyl radical, and an aluminum hydrocarbyl radical.

5. The catalyst of claim 1 wherein R'' is a methyl, ethyl, isopropyl, cyclopropyl, dimethylsilyl, methylene or ethylene radical.

6. The catalyst of claim 1 wherein n is 0.

7. The catalyst of claim 1 wherein $R''(CpR_n)(CpR'_m)$ forms an isopropyl(cyclopentadienyl-1-fluorenyl) radical.

8. The catalyst of claim 1 wherein $R_m$ is selected such that $(CpR'_m)$ forms a fluorenyl, indenyl, tetra-, tri-, or dialkyl substituted cyclopentadienyl radical and $R_n$ is selected such that $(CpR_n)$ forms an alkyl substituted or unsubstituted cyclopentadienyl radical.

9. The catalyst of claim 1 further comprising an aluminum compound selected from the group consisting of alumoxanes, alkyl aluminums and mixtures thereof.

10. The catalyst of claim 9 comprising an isolated complex of the metallocene catalyst and the aluminum compound.

11. A process for preparing a bridged metallocene catalyst having sterically different cyclopentadienyl rings comprising:
(a) contacting a cyclopentadiene or substituted cyclopentadiene with fulvene or a substituted fulvene under reaction conditions sufficient to produce a bridged dicyclopentadiene or substituted dicyclopentadiene, and
(b) contacting said bridged dicyclopentadiene or substituted dicyclopentadiene with a metal compound of the formula $MeQ_k$ under reaction conditions sufficient to complex the bridged dicyclopentadiene or substituted dicyclopentadiene with the metal compound to produce a bridged metallocene, wherein Me is a group 4b, 5b or 6b metal from the Periodic Table of Elements, each Q is a hydrocarbyl radical having 1-20 carbon atoms or is a halogen and $0 \leq k \leq 4$.

12. The process of claim 11 wherein the contacting of step (b) is performed in a chlorinated solvent.

* * * * *

UNITED STATES PATENT AND TRADEMARK OFFICE
CERTIFICATE OF CORRECTION

PATENT NO. : 4,892,851

DATED : January 9, 1990

INVENTOR(S) : John A. Ewen, Houston; Abbas Razavi, Seabrook, both of Tex.

It is certified that error appears in the above-identified patent and that said Letters Patent is hereby corrected as shown below:

On the title page, item [75] should read:
        Inventor: Abbas Razavi, Seabrook, Tex.

Signed and Sealed this

Fourteenth Day of January, 1997

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 4,892,851

DATED : January 09, 1990

INVENTOR(S) : John A. Ewen and Abbas Razavi

It is certified that error appears in the above-identified patent and that said Letters Patent is hereby corrected as shown below:

All reference to Certificate of Correction appearing in Official Gazette of January 14, 1997 should be deleted since no certificate of correction was granted.

Signed and Sealed this

Twenty-fifth Day of March, 1997

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 4,892,851
DATED : January 9, 1990
INVENTOR(S) : Abbas Razavi and John A. Ewen It is certified that error appears in the above-identified patent and that said Letters Patent is hereby corrected as shown below:

Title page,
Item [75], Inventors, should read -- Abbas Razavi, Seabrook, TX. and John A. Ewen, Houston, TX. --

Signed and Sealed this

Twenty-eighth Day of October, 2003

JAMES E. ROGAN
*Director of the United States Patent and Trademark Office*